United States Patent
Kawakubo et al.

(10) Patent No.: US 10,344,162 B2
(45) Date of Patent: Jul. 9, 2019

(54) POLYCARBONATE RESIN COMPOSITION HAVING EXCELLENT THERMAL DECOMPOSITION RESISTANCE

(71) Applicant: KANEKA CORPORATION, Osaka-shi, Osaka (JP)

(72) Inventors: Hidekazu Kawakubo, Osaka (JP); Kazunori Saegusa, Osaka (JP); Kazushi Nakatani, Osaka (JP)

(73) Assignee: KANEKA CORPORATION, Osaka-shi, Osaka (JP)

( * ) Notice: Subject to any disclaimer, the term of this patent is extended or adjusted under 35 U.S.C. 154(b) by 53 days.

(21) Appl. No.: 15/578,883

(22) PCT Filed: Jun. 3, 2016

(86) PCT No.: PCT/JP2016/066681
§ 371 (c)(1),
(2) Date: Dec. 1, 2017

(87) PCT Pub. No.: WO2016/195100
PCT Pub. Date: Dec. 8, 2016

(65) Prior Publication Data
US 2018/0155543 A1  Jun. 7, 2018

(30) Foreign Application Priority Data
Jun. 4, 2015 (JP) .................. 2015-114228

(51) Int. Cl.
*C08L 69/00* (2006.01)
*C08L 67/00* (2006.01)
(Continued)

(52) U.S. Cl.
CPC .............. *C08L 69/00* (2013.01); *C08L 57/10* (2013.01); *C08L 67/00* (2013.01); *C08L 101/00* (2013.01);
(Continued)

(58) Field of Classification Search
CPC .......... C08L 69/00; C08L 67/00; C08L 57/10; C08L 2205/03; C08L 2201/08; G01N 5/04
(Continued)

(56) References Cited

U.S. PATENT DOCUMENTS 4,687,819 A * 8/1987 Quinn ................ C08L 67/02
525/425
2015/0099106 A1  4/2015 Kawakubo et al.

FOREIGN PATENT DOCUMENTS

JP  2010-126706 A  6/2010
JP  2010-254739 A  11/2010
(Continued)

OTHER PUBLICATIONS

International Search Report of PCT/JP2016/066681 dated Aug. 9, 20116.

*Primary Examiner* — William K Cheung
(74) *Attorney, Agent, or Firm* — Sughrue Mion, PLLC (57) ABSTRACT

Provided is a polycarbonate resin composition containing 1-20 parts by weight of an amorphous thermoplastic resin having a glass transition temperature of not lower than 110° C., and 1-50 parts by weight of plate-shaped fillers having a number average major axis length of 0.5-45 μm, with respect to 100 parts by weight of a matrix resin component containing 35-95 wt % of a polycarbonate resin and 5-65 wt % of a thermoplastic polyester resin.

7 Claims, 3 Drawing Sheets

(51) Int. Cl.
  *C08L 101/00* (2006.01)
  *C08L 57/10* (2006.01)
  *G01N 5/04* (2006.01)
(52) U.S. Cl.
  CPC ....... *C08L 2201/08* (2013.01); *C08L 2205/03* (2013.01); *G01N 5/04* (2013.01)
(58) Field of Classification Search
  USPC ........................................................ 525/145
  See application file for complete search history.

(56) References Cited

FOREIGN PATENT DOCUMENTS

| | | |
|---|---|---|
| JP | 2012-236957 A | 12/2012 |
| WO | 2013/162043 A1 | 10/2013 |

* cited by examiner

FIG. 3

POLYCARBONATE RESIN COMPOSITION HAVING EXCELLENT THERMAL DECOMPOSITION RESISTANCE

CROSS REFERENCE TO RELATED APPLICATIONS

This application is a National Stage of International Application No. PCT/JP2016/066681 filed Jun. 3, 2016, claiming priority based on Japanese Patent Application No. 2015-114228 filed Jun. 4, 2015, the contents of all of which are incorporated herein by reference in their entirety.

TECHNICAL FIELD

The present invention relates to a polycarbonate resin composition, and a molded article using the resin composition.

BACKGROUND ART

A polycarbonate resin is conventionally known as a resin having the highest impact-resistance of engineering plastics and having high heat resistance, and therefore, is used in various fields thanks to these advantages. However, the polycarbonate resin has drawbacks such as low chemical resistance, poor molding workability, and thickness dependence of impact strength.

Meanwhile, thermoplastic polyester resins have high chemical resistance and good molding workability, but have drawbacks such as low impact resistance and poor dimensional stability.

Various resin compositions have been proposed which utilize the advantages of these materials to compensate for their drawbacks. For example, attempts have been made to simultaneously satisfy impact resistance, heat resistance, chemical resistance, weather resistance, moldability, etc., that are required for automotive parts, etc.

At present, resin members that are formed as resin molded articles (also hereinafter simply referred to as "molded article") are commonly substituted for metal members in various industrial fields. For example, for members, for electrical appliances, such as housings of mobile telephones and personal computers, and members, for vehicles, such as fenders, door panels, and rear door panels of automobiles, reduction in weight is strongly required, and a metal may be replaced by a resin in a larger area, and therefore, attempts have been made to increase the sizes of resin molded articles and decrease the thicknesses of shapes of molded articles by metal being replaced by resin. Increase of the size of the molded article and decrease of the thickness thereof require the use of a molding machine larger than conventional ones. Therefore, resins are likely to undergo thermal decomposition due to thermal hysteresis of the resins during molding, and shear heat generation during die filling, so that defective appearance (flash), etc., occurs on the molded article surface due to thermal decomposition gas. Flash is also called "silver" or "silver streaks."

To reduce the thermal decomposition of a resin, Patent Literature 1 proposes a resin composition containing a polycarbonate resin, and a polyester-polyether copolymer modified with a polyalkylene glycol of a bisphenol, etc. The resin composition has excellent fluidity, and allows shear heat generation to be reduced even in a thin shape. Therefore, when the resin composition is used as a molding material, a large-sized or thin molded article can be obtained without defective appearance. However, under current circumstances that enhanced increase in sizes of molded articles and enhanced decrease in thicknesses thereof are required, and molded articles are expected to be used in environments having even higher temperature, etc., a resin composition that can be used to provide a molded article having enhanced heat resistance and thermal decomposition resistance is needed.

CITATION LIST

Patent Literature

[PTL 1] International Publication WO 2013/162043

SUMMARY OF THE INVENTION

Problems to be Solved by the Invention

It is an object of the present invention to provide a resin composition which contains a polycarbonate resin and a thermoplastic polyester resin, which has excellent heat resistance and thermal decomposition resistance, and a low linear expansion coefficient, and which can be used to provide a molded article having good appearance and good appearance after coating, and in which these characteristics are well balanced.

Solution to the Problems

To achieve the above object, the present inventors have extensively studied to find that a resin composition obtained by adding a specific amount of an amorphous thermoplastic resin having a glass transition temperature of not lower than 110° C. and a specific amount of plate-shaped fillers having a number average major axis length of not less than 0.5 µm and not more than 45 µm, to a matrix resin component containing a polycarbonate resin and a thermoplastic polyester resin, has excellent heat resistance (deflection temperature under load), excellent thermal decomposition resistance (measurement of weight reduction using a differential thermal/thermogravimetric simultaneous measurement device), and a low linear expansion coefficient, that are suitable for large-sized molded articles and thin molded articles which are used as automotive members, etc. The present inventors also have found that the resin composition can be used to provide a molded article that has good appearance and good appearance after coating because the occurrence of flash (silver streaks) on the surface of the molded article due to decomposition gas is significantly reduced, and that the resin composition also has the above characteristics in a well-balanced manner. Based on the findings, the present invention has been made.

Specifically, the present invention is as described below.

1) A polycarbonate resin composition including: 100 parts by weight of a resin component containing not less than 35 wt % and not more than 95 wt % of a polycarbonate resin (A), and not less than 5 wt % and not more than 65 wt % of a thermoplastic polyester resin (B); not less than 1 part by weight and not more than 20 parts by weight of an amorphous thermoplastic resin (C) having a glass transition temperature of not lower than 110° C.; and not less than 1 part by weight and not more than 50 parts by weight of plate-shaped fillers (D) having a number average major axis length of not less than 0.5 µm and not more than 45 µm.

2) The polycarbonate resin composition according to 1), in which the amorphous thermoplastic resin (C) is incompatible with the polycarbonate resin (A) and is incompatible with the thermoplastic polyester resin (B).

3) The polycarbonate resin composition according to 1) or 2), in which the amorphous thermoplastic resin (C) is at least one amorphous resin selected from the group consisting of polyphenylene ether resins, polyarylate resins, polyetherimide resins, polysulfone resins, and modified styrene resins.

4) The polycarbonate resin composition according to any one of 1) to 3), in which the polycarbonate resin composition has a deflection temperature under load of not lower than 110° C. and not higher than 120° C.

5) The polycarbonate resin composition according to any one of 1) to 4), in which the polycarbonate resin composition has a weight reduction start temperature of not lower than 410° C. and not higher than 420° C. as measured using a differential thermal/thermogravimetric simultaneous measurement device.

6) A molded article comprising the polycarbonate resin composition according to 1) to 5).

7) The molded article according to 6), in which the molded article has a maximum projected area of not less than 10,000 mm² and not more than 10,000,000 mm².

Advantageous Effects of the Invention

The polycarbonate resin composition of the present invention has excellent heat resistance (deflection temperature under load), excellent thermal decomposition resistance (measurement of weight reduction using a differential thermal/thermogravimetric simultaneous measurement device), and a low linear expansion coefficient, and can be used to provide a molded article that has good appearance and good appearance after coating.

DESCRIPTION OF EMBODIMENTS (Polycarbonate Resin Composition)

A polycarbonate resin composition according to the present invention (may also be hereinafter simply referred to as "the resin composition of the present invention") contains: 100 parts by weight of a resin component (may also be hereinafter referred to as a "matrix resin component") containing not less than 35 wt % and not more than 95 wt % of a polycarbonate resin (A), and not less than 5 wt % and not more than 65 wt % of a thermoplastic polyester resin (B); not less than 1 part by weight and not more than 20 parts by weight of an amorphous thermoplastic resin (C) having a glass transition temperature of not lower than 110° C.; and not less than 1 part by weight and not more than 50 parts by weight of plate-shaped fillers (D) having a number average major axis length of not less than 0.5 μm and not more than 45 μm. The total of the polycarbonate resin (A) and the thermoplastic polyester resin (B) in the matrix resin component preferably accounts for 100 parts by weight. More preferably, the content of the amorphous thermoplastic resin (C) having a glass transition temperature of not lower than 110° C. is not less than 1 part by weight and not more than 20 parts by weight, and the content of the plate-shaped fillers (D) having a number average major axis length of not less than 0.5 μm and not more than 45 μm is not less than 1 part by weight and not more than 50 parts by weight, with respect to a total of 100 parts by weight of the polycarbonate resin (A) and the thermoplastic polyester resin (B).

In order to further improve the impact resistance, the polycarbonate resin composition of the present invention preferably contains not less than 0.5 parts by weight and not more than 40 parts by weight of an impact modifier (E) with respect to 100 parts by weight of the matrix resin component. The content of the impact modifier (E) is more preferably not less than 1 part by weight and not more than 20 parts by weight in terms of heat resistance, rigidity, moldability, etc., and is even more preferably not less than 2 parts by weight and not more than 10 parts by weight in order to obtain impact strength and heat resistance that are required when a molded article made of the resin composition of the present invention is used as a vehicle member that is a preferable application.

In order to further improve the heat resistance, the resin composition of the present invention preferably has a deflection temperature under load of not lower than 110° C. and not higher than 120° C. as measured under a load of 1.80 MPa according to ISO75. In order to further improve the thermal decomposition resistance, the resin composition of the present invention has a weight reduction start temperature of not lower than 410° C. and not higher than 420° C. as measured using a differential thermal/thermogravimetric simultaneous measurement device. When the resin composition of the present invention has a deflection temperature under load of not lower than 110° C. and not higher than 120° C. and a weight reduction start temperature of not lower than 410° C. and not higher than 420° C., the resin composition of the present invention can simultaneously have higher levels of characteristics, such as heat resistance, thermal decomposition resistance, a low linear expansion coefficient, appearance, and coating appearance, in a well-balanced manner. The above deflection temperature under load and weight reduction start temperature can be achieved by selecting components and their contents on the basis of the description of the present specification.

The resin composition of the present invention features the dispersed state of each of the components (A) to (D). This characteristic feature can be seen from, for example, a transmission electron microscope photograph of the resin composition of the present invention that is prepared in the form of a pellet. Specifically, the dispersed form as observed in the electron microscope photograph is characteristic in that, in the pellet, the thermoplastic polyester resin (B) (islands) and the amorphous thermoplastic resin (C) (islands) are each independently dispersed in the polycarbonate resin (A) (sea), and all or most of the plate-shaped fillers (D) are covered by the thermoplastic polyester resin (B). Thus, the resin composition according to an embodiment of the present invention has a sea/island/island structure in which the thermoplastic polyester resin (B) and the amorphous thermoplastic resin (C) are each independently dispersed in the polycarbonate resin (A), and has a dispersion structure in which the plate-shaped fillers (D) are mainly present in the thermoplastic polyester resin (B).

Figure 1:
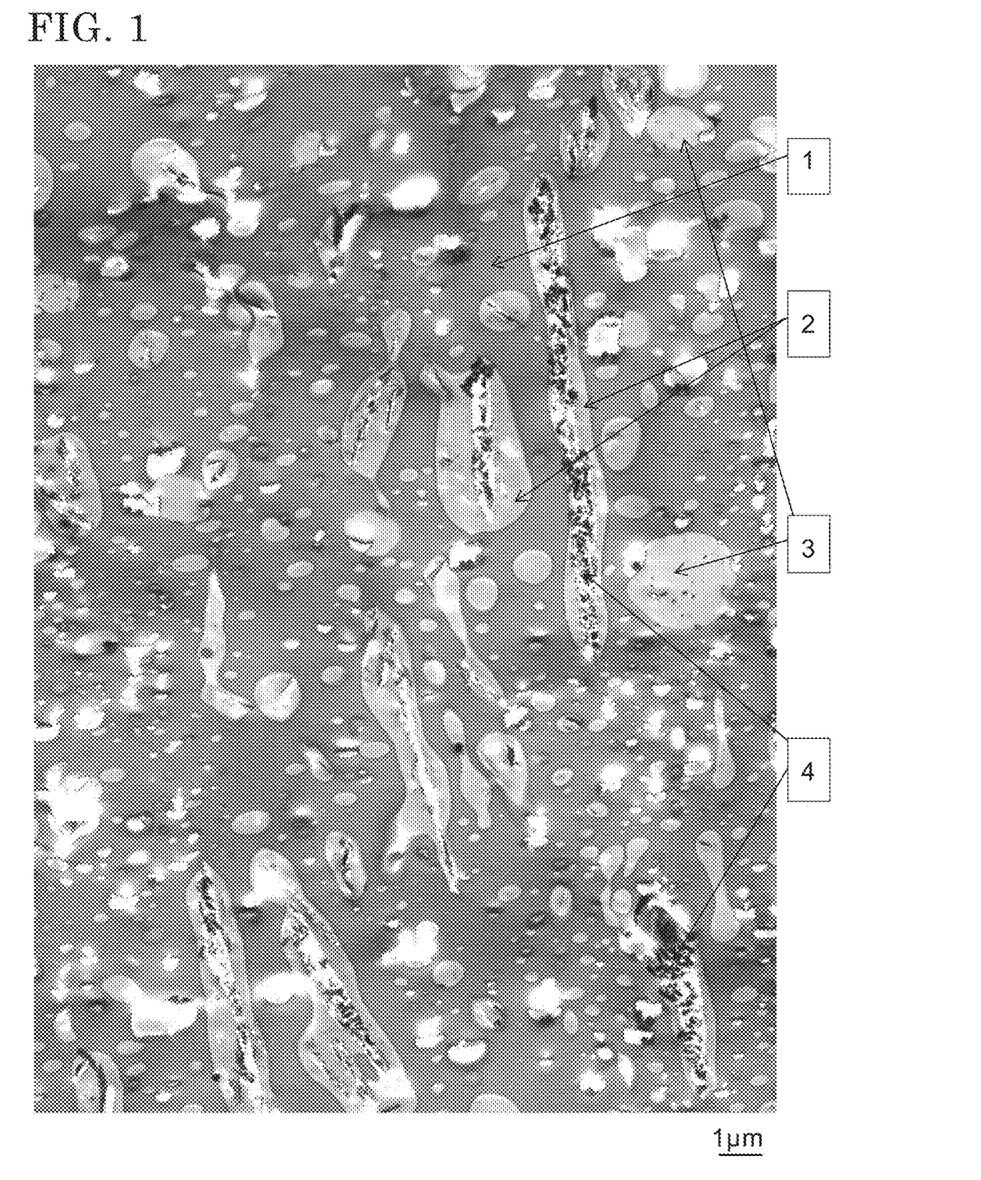
FIG. 1 is a transmission electron microscope photograph of a pellet of a resin composition obtained in Example 2.
Figure 2:
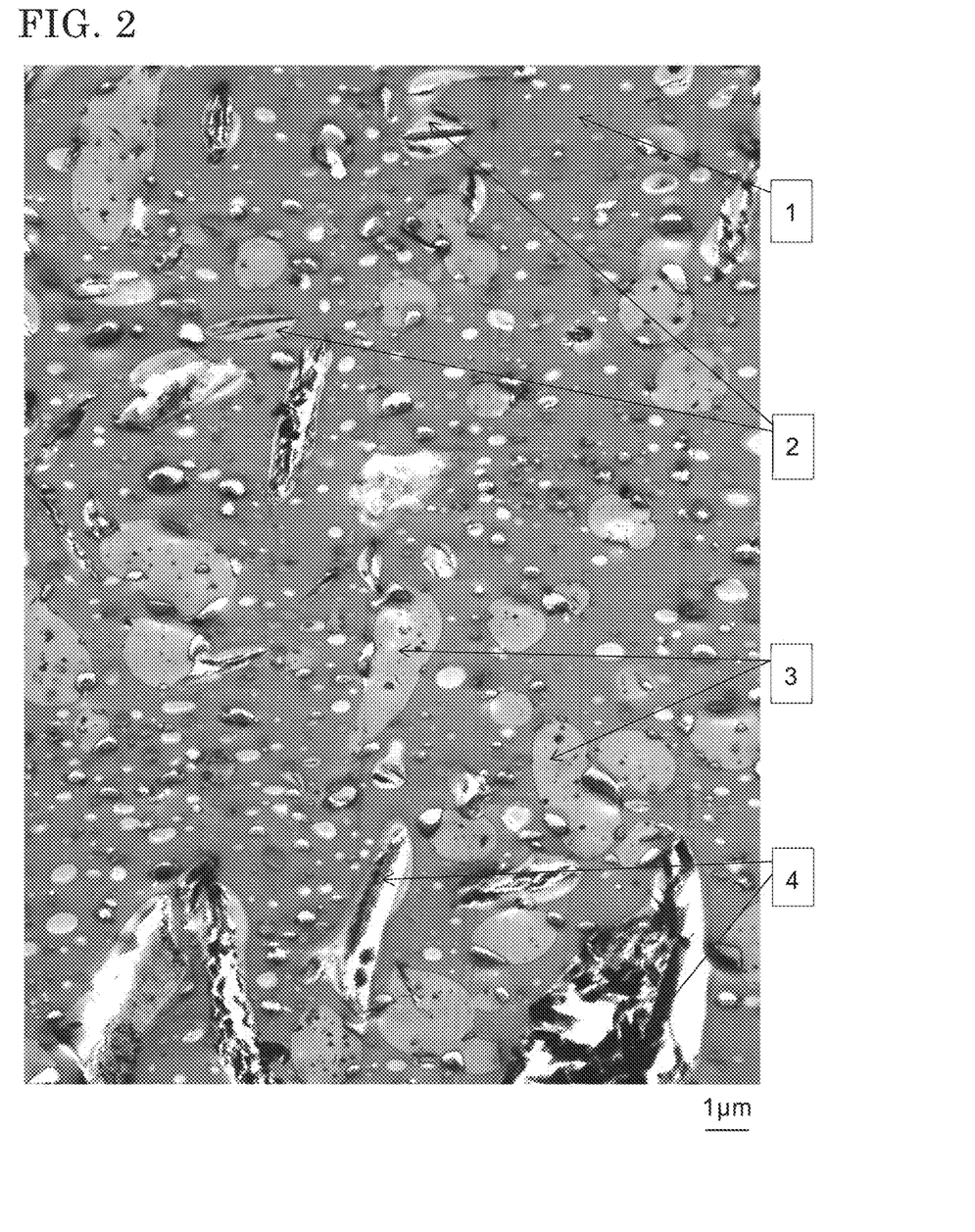
FIG. 2 is a transmission electron microscope photograph of a pellet of a resin composition obtained in Example 6.

FIG. 1 and FIG. 2 each show a transmission electron microscope photograph (at 10,000× magnification) indicating a sea/island/island structure in which relatively light gray portions (islands) 2 and 3 are each independently present in a relatively dark gray portion (sea) 1 extending throughout the entirety of the electron microscope photograph. The gray portions 2, which are each an elongated region extending in generally one direction, may cover and include a plurality of black portions 4. The gray portions 3, which are each a region in the shape of generally an approximate ellipse to a perfect circle, do not include the black portion 4. The gray portion 1 indicates the polycarbonate resin (A), the gray portion 2 indicates the thermoplastic polyester resin (B) (polyethylene terephthalate resin), the gray portion 3 indicates the amorphous thermoplastic resin (C) (polyphenylene ether resin), and the black portion 4 indicates an aggregate of a plurality of plate-shaped fillers (D). It is considered that such a dispersion structure is one factor for obtaining the effect of the present invention.

Each of the components of the resin composition of the present invention will now be described in greater detail. In the description herein, the term "not less than, not more than" may be replaced by the term "-", or vice versa. For example, "not less than 10 parts by weight and not more than 90 parts by weight" means "10-90 parts by weight", "110-120° C." means "not lower than 110° C. and not higher than 120° C.", and "0.2-0.8 dl/g" means "not less than 0.2 dl/g and not more than 0.8 dl/g". The unit of a numerical range is not limited to the units described here ("parts by weight", "° C.", and "dl/g").

In the resin composition of the present invention, the matrix resin component contains the polycarbonate resin (A) and the thermoplastic polyester resin (B).

<Polycarbonate Resin (A)>

The polycarbonate resin (A) for use in the present invention, which is a polycarbonate resin derived from a compound having two phenolic hydroxyl groups (may also be hereinafter referred to as a "divalent phenol"), is typically obtained by a reaction between the divalent phenol and phosgene, or between the divalent phenol and a carbonate diester.

The above divalent phenol is particularly preferably, but not limited to, bisphenol A.

The polycarbonate resin (A) preferably has a viscosity average molecular weight within the range of 10,000-60,000, more preferably 12,000-30,000, and even more preferably 15,000-20,000 in terms of impact resistance, chemical resistance, molding workability, etc.

The content of the polycarbonate resin (A) is not less than 35 wt % and not more than 95 wt %, preferably not less than 40 wt % and not more than 95 wt % of the total amount of the matrix resin component. The content of the polycarbonate resin (A) is more preferably not less than 60 wt % and not more than 90 wt %, even more preferably not less than 70 wt % and not more than 80 wt %, of the total amount of the matrix resin component in terms of balance between fluidity, heat resistance, and mechanical properties.

<Thermoplastic Polyester Resin (B)>

The thermoplastic polyester resin (B) according to the present invention refers to a saturated polyester resin that is obtained using a divalent acid, such as terephthalic acid or a derivative thereof having an ability to form an ester, as an acid component, and a glycol having 2-10 carbon atoms, another divalent alcohol, a derivative thereof having an ability to form an ester, or the like, as a glycol component.

Of saturated polyester resins, polyalkylene terephthalate resins are preferable because of their excellent balance between moldability, mechanical properties, electrical properties, heat resistance, etc. Specific examples of polyalkylene terephthalate resins include polyethylene terephthalate resin, polybutylene terephthalate resin, polypropylene terephthalate resin, and polyhexamethylene terephthalate resin. Of them, polyethylene terephthalate resin is particularly preferable because of its excellent heat resistance and chemical resistance.

The content of the thermoplastic polyester resin (B) of the present invention is not less than 5 wt % and not more than 65 wt %, preferably not less than 5 wt % and not more than 60 wt %, of the total amount of the matrix resin component. The content of the thermoplastic polyester resin (B) of the present invention is more preferably not less than 10 wt % and not more than 40 wt %, even more preferably not less than 20 wt % and not more than 30 wt %, of the total amount of the matrix resin component in terms of balance between fluidity, chemical resistance, and heat resistance.

The thermoplastic polyester resin (B) for use in the present invention may be optionally a copolymer containing another component in an amount that does not significantly reduce its physical properties. As a component in the copolymer, a known acid component, alcohol component, and/or phenol component, or a derivative thereof having an ability to form an ester, may be used.

Examples of the copolymerizable acid component include divalent or higher-valent aromatic carboxylic acids having 8-22 carbon atoms, divalent or higher-valent aliphatic carboxylic acids having 4-12 carbon atoms, divalent or higher-valent alicyclic carboxylic acids having 8-15 carbon atoms, and derivatives thereof having an ability to form an ester. Specific examples of the copolymerizable acid component include terephthalic acid, isophthalic acid, naphthalenedicarboxylic acid, bis(p-carbodiphenyl)methane anthracenedicarboxylic acid, 4-4'-diphenylcarboxylic acid, 1,2-bis(phenoxy)ethane-4,4'-dicarboxylic acid, 5-sodiumsulfoisophthalic acid, adipic acid, sebacic acid, azelaic acid, dodecanedioic acid, maleic acid, trimesic acid, trimellitic acid, pyromellitic acid, 1,3-cyclohexanedicarboxylic acid, 1,4-cyclohexanedicarboxylic acid, and derivatives thereof having an ability to form an ester. These may be used alone or in combination. Of them, terephthalic acid, isophthalic acid, and naphthalenedicarboxylic acid are preferable because of the excellent physical properties and handling of the resulting resin, and easy reaction.

Examples of the copolymerizable alcohol and/or phenol components include divalent or higher-valent aliphatic alcohols having 2-15 carbon atoms, divalent or higher-valent alicyclic alcohols having 6-20 carbon atoms, divalent or higher-valent aromatic alcohols having 6-40 carbon atoms, phenol, and derivatives thereof having an ability to form an ester. Specific examples of the copolymerizable alcohol and/or phenol components include compounds such as ethylene glycol, propanediol, butanediol, hexanediol, decanediol, neopentyl glycol, cyclohexanedimethanol, cyclohexanediol, 2,2'-bis(4-hydroxyphenyl)propane, 2,2'-bis(4-hydroxycyclohexyl)propane, hydroquinone, glycerin, pentaerythritol, and derivatives thereof having an ability to form an ester, and cyclic esters such as ε-caprolactone, etc. Of them, ethylene glycol and butanediol are preferable because of the excellent physical properties and handling of the resulting resin, and easy reaction.

A polyalkylene glycol unit may be partially copolymerized. Specific examples of the polyoxyalkylene glycol include polyethylene glycol, polypropylene glycol, polytetramethylene glycol, and random or block copolymers thereof, and modified polyoxyalkylene glycols, such as adducts of bisphenol compounds with alkylene glycols (polyethylene glycol, polypropylene glycol, polytetramethylene glycol, and random or block copolymers thereof, etc.). Of them, an adduct of bisphenol A with polyethylene glycol that has a molecular weight of 500-2000 is preferable because, for example, the thermal stability is good during copolymerization, and the heat resistance of a molded article obtained from the resin composition of the present invention is less likely to decrease.

These thermoplastic polyester resins (B) may be used alone or in combination.

The thermoplastic polyester resin (B) of the present invention may be obtained by a known polymerization technique, such as melt polycondensation, solid-phase polycondensation, solution polymerization, etc. In addition, one or more of compounds such as phosphoric acid, phosphorous acid, hypophosphorous acid, monomethyl phosphate, dimethyl phosphate, trimethyl phosphate, methyldiethyl phosphate, triethyl phosphate, triisopropyl phosphate, tributyl phosphate, and triphenyl phosphate, may be added during polymerization in order to improve the color tone of the resin.

The molecular weight of the thermoplastic polyester resin (B) for use in the present invention is not particularly limited, and is preferably such that the logarithmic viscosity (IV) thereof is 0.3-1.00 dL/g at 25° C. and 0.5 g/dl in a mixture solution of phenol and tetrachloroethane having a weight ratio of 1/1. The IV value is more preferably within the range of 0.40-0.85 dl/g in terms of an improved balance between moldability, heat resistance, and low linear expansion.

In the resin composition of the present invention, the matrix resin component typically contains 35-95 wt % of the polycarbonate resin, and 5-65 wt % of the thermoplastic polyester resin, preferably 40-95 wt % of the polycarbonate resin, and 5-60 wt % of the thermoplastic polyester resin, more preferably 60-90 wt % of the polycarbonate resin, and 10-40 wt % of the thermoplastic polyester resin, and even more preferably 70-80 wt % of the polycarbonate resin, and 20-30 wt % of the thermoplastic polyester resin.

The resin composition of the present invention contains the amorphous thermoplastic resin (C) and the plate-shaped fillers (D) as essential components, together with the matrix resin component, and may optionally contain at least one component selected from the group consisting of the impact modifier (E), stabilizers, and resin additives.

<Amorphous Thermoplastic Resin (C)>

The amorphous thermoplastic resin (C) in the present invention has a glass transition temperature of not lower than 110° C. For example, the amorphous thermoplastic resin (C) is preferably at least one selected from the group consisting of polyetherimide resins, polyphenylene ether resins, polysulfone resins, such as polysulfone, polyphenylsulfone, and polyethersulfone, polyarylate resins, and modified styrene resins. By adding the amorphous thermoplastic resin (C), the thermal decomposition resistance and heat resistance can be improved. Further, a mixture, such as a polymer alloy or a polymer blend, that contains the amorphous thermoplastic resin (C) and another polymer may be used.

The amorphous thermoplastic resin (C) in the present invention is preferably incompatible with the polycarbonate resin (A) and the thermoplastic polyester (B) in terms of thermal decomposition resistance. In other words, the amorphous thermoplastic resin (C) that is incompatible with the polycarbonate resin (A) and the thermoplastic polyester resin (B) is preferable. It is considered that, in the present invention, the amorphous thermoplastic resin (C) is not sufficiently compatible with the matrix resin component, and therefore, the sea/island structure is formed, so that the resin composition of the present invention exhibits the above-described preferable characteristics at a high level and in a well-balanced manner.

In the present invention, the incompatibility and compatibility are determined from the glass transition temperature of a resin composition (X) obtained by kneading: the polycarbonate resin (A) or the thermoplastic polyester resin (B); and the amorphous thermoplastic resin (C) at (a weight ratio of) 1:1 at 280-330° C. The glass transition temperature is measured by differential scanning calorimetry (DSC) while the temperature is increased at 10° C./min.

The incompatibility is determined when glass transition temperatures attributed to the glass transition temperature (A-Tg) (° C.) of the polycarbonate resin (A) or the glass transition temperature (B-Tg) (° C.) of the thermoplastic polyester resin (B), and the glass transition temperature (C-Tg) (° C.) of the amorphous thermoplastic resin (C), in the resin composition (X), are within ±20° C., more preferably ±15° C., from the respective glass transition temperatures before kneading.

The compatibility is determined when, in the resin composition (X), none of glass transition temperatures attributed to (A-Tg) (° C.) or (B-Tg) (° C.) and (C-Tg) (° C.) is observed, and a single glass transition temperature is observed, or (A-Tg) (° C.) or (B-Tg) (° C.) and (C-Tg) (° C.) in the resin composition (X) do not satisfy the above compatibility determining condition.

The amorphous thermoplastic resin (C) is more preferably polyphenylene ether resins and polyarylate resins, particularly preferably polyphenylene ether resins, in terms of thermal decomposition resistance and fluidity. Polyetherimide resins are more preferable in terms of heat resistance. Modified styrene resins are also more preferable in terms of the surface roughness of a molded article that has an influence on the appearance after coating (coating appearance) of the molded article.

In the present invention, the polyetherimide resin refers to a polymer containing an aliphatic, alicyclic, or aromatic ether unit and a cyclic imide group as a repeating unit, and is not particularly limited if the polyetherimide resin is a polymer having melt moldability. As long as the advantages of the present invention are not inhibited, the main chain of the polyetherimide may contain a structural unit, such as an aromatic ester unit, an aliphatic ester unit, an alicyclic ester unit, an oxycarbonyl unit, etc., in addition to the cyclic imide and the ether bond.

In the present invention, the polyphenylene ether resin refers to a homopolymer or copolymer having a structural unit represented by general formula 1 indicated below.

[Chemical formula 1]

General formula 1

(In the formula, each of two $R_1$, which may be the same or different, represents a hydrogen atom, a primary alkyl group, a secondary alkyl group, an aryl group, an aminoalkyl group, or a hydrocarbonoxy group, each of two $R_2$, which may be the same or different, represents a primary alkyl group, a secondary alkyl group, an aryl group, or an amino group, and n represents an integer of not less than 10.)

Examples of the primary alkyl group represented by $R_1$ or $R_2$ include chain primary alkyl groups having 1-7 carbon atoms, such as methyl, ethyl, n-propyl, n-butyl, n-amyl, isoamyl, 2-methylbutyl, n-hexyl, 2,3-dimethylbutyl, 2-methylpentyl, 3-methylpentyl, 4-methylpentyl, n-heptyl group, etc. A preferable example of the secondary alkyl group is isopropyl, sec-butyl, or 1-ethylpropyl. A preferable example of the polyphenylene ether resin that is a homopolymer is a homopolymer containing 2,6-dimethyl-1,4-phenylene ether units. A preferable example of the copolymer is a random copolymer containing a combination of a structural unit represented by general formula 1 and a 2,3,6-trimethyl-1,4-phenylene ether unit.

The above polyphenylene ether resin preferably has an intrinsic viscosity of 0.2-0.8 dl/g as measured in chloroform at 30° C., more preferably 0.25-0.7 dl/g. Particularly preferably, the polyphenylene ether resin having an intrinsic viscosity of 0.3-0.6 dl/g is suitably used. The polyphenylene ether resin having an intrinsic viscosity of less than 0.2 dl/g is not preferable, because such a polyphenylene ether resin is difficult to industrially produce, and the resin composition of the present invention has an insufficient impact resistance. The polyphenylene ether resin having an intrinsic viscosity exceeding 0.8 dl/g leads to a large amount of gel components, resulting in deterioration in the appearance of a molded article formed of the resin composition of the present invention.

The polyphenylene ether resin may contain up to 35 wt % of a styrene resin that is compatible with the polyphenylene ether resin, with respect to the polyphenylene ether resin, in order to reduce the apparent viscosity thereof. Examples of such a styrene resin include polystyrene, styrene-butadiene copolymer, etc. When the styrene resin content exceeds 35 wt %, the heat resistance is reduced compared to polyphenylene ether, which is not preferable.

In the present invention, the polysulfone resin refers to a thermoplastic resin having, as a main chain, an aromatic ring group and a sulfone group that links the aromatic ring group to the main chain. Such a kind of thermoplastic resins are generally divided into polysulfones, polyethersulfones, and polyphenylsulfones.

In the present invention, the polyarylate resin refers to a resin containing an aromatic dicarboxylic acid and a bisphenol as repeating units.

Specific examples of the bisphenol include 2,2-bis(4-hydroxyphenyl)propane, 2,2-bis(4-hydroxy-3,5-dimethylphenyl)propane, 2,2-bis(4-hydroxy-3,5-dibromophenyl)propane, 2,2-bis(4-hydroxy-3,5-dichlorophenyl)propane, 4,4'-dihydroxydiphenyl sulfone, 4,4'-dihydroxydiphenyl ether, 4,4'-dihydroxydiphenyl sulfide, 4,4'-dihydroxydiphenyl ketone, 4,4'-dihydroxydiphenyl methane, 1,1-bis(4-hydroxyphenyl)cyclohexane, etc. These compounds may be used alone or as a mixture of two or more kinds thereof. In particular, 2,2-bis(4-hydroxyphenyl)propane is economically preferable.

Specific examples of the aromatic dicarboxylic acid include terephthalic acid, isophthalic acid, orthophthalic acid, 1,5-naphthalenedicarboxylic acid, 2,6-naphthalenedicarboxylic acid, diphenic acid, 4,4'-dicarboxydiphenyl ether, bis(p-carboxyphenyl)alkane, 4,4'-dicarboxydiphenyl sulfone, etc. Of them, terephthalic acid and isophthalic acid are preferable. These aromatic dicarboxylic acids may be used alone or in combination.

In the present invention, the modified styrene resin refers to at least one selected from the group consisting of copolymers of a styrene resin containing a structural unit derived from an aromatic vinyl compound, and another vinyl monomer (I) copolymerizable therewith, and copolymers of the aromatic vinyl compound and another vinyl monomer (II) copolymerizable therewith.

The aromatic vinyl compound refers to an aromatic vinyl compound in which a vinyl group or an alkylethenyl group (alkyl group-substituted vinyl group) is linked to a benzene ring. Specific examples of the aromatic vinyl compound include styrene, α-methylstyrene, o-methylstyrene, p-methylstyrene, vinylxylene, ethylstyrene, dimethylstyrene, p-tert-butylstyrene, vinylnaphthalene, methoxystyrene, monobromostyrene, dibromostyrene, fluorostyrene, tribromostyrene, etc. In particular, styrene is preferable. These aromatic vinyl compounds may be used alone or in combination.

Examples of the styrene resin containing a structural unit derived from an aromatic vinyl compound include a homopolymer or homologs polymer of the aromatic vinyl compound, a copolymer of the aromatic vinyl compound and another vinyl monomer (III) copolymerizable therewith, etc. Specific preferable examples of the vinyl monomer (III) in the copolymer include vinyl cyanide monomers and (meth)acrylic acid ester monomers. Examples of the vinyl cyanide monomers include vinyl cyanide compounds such as acrylonitrile and methacrylonitrile. In particular, acrylonitrile is preferable. Examples of the (meth)acrylic acid ester monomers include (meth)acrylic acid ester compounds such as (meth)acrylic acid $C_{1-4}$ alkyl ester.

When the modified styrene resin is a copolymer of a styrene resin and another vinyl monomer (I) copolymerizable therewith as described above, examples of the vinyl monomer (I) include epoxy group-containing methacrylic acid esters such as glycidyl methacrylate, maleimide monomers such as maleimide and N-phenylmaleimide, α,β-unsaturated carboxylic acids and anhydrides thereof such as acrylic acid, methacrylic acid, maleic acid, maleic anhydride, phthalic acid, and itaconic acid, etc. Of them, maleimide monomers are preferable, and N-phenylmaleimide is more preferable, in terms of not only the heat resistance and thermal decomposition resistance, but also the coating appearance, of a molded article. The vinyl monomers (I) may be used alone or in combination.

When the modified styrene resin is a copolymer of the above aromatic vinyl compound and another vinyl monomer (II) copolymerizable therewith as described above, as the vinyl monomer (II), one or more selected from the monomers described above as the specific examples of the vinyl monomers (I) and (III) may be used. Of them, vinyl cyanide monomers, (meth)acrylic acid ester monomers, maleimide monomers, etc., are preferable.

Of the modified styrene resins, a copolymer containing a structural unit derived from styrene and a structural unit derived from N-phenylmaleimide, a copolymer containing a structural unit derived from styrene, a structural unit derived from N-phenylmaleimide, and a structural unit derived from acrylonitrile, a copolymer containing a structural unit derived from styrene, a structural unit derived from N-phenylmaleimide, and a structural unit derived from alkyl methacrylate (preferably, methyl methacrylate), etc., are more preferable. When these copolymers are added, together with the plate-shaped fillers (D), to the matrix resin component containing the polycarbonate resin (A) and the thermoplastic polyester resin (B) as in the present invention, not only the heat resistance can be improved, but also the surface roughness of the resulting molded article can be reduced, and therefore, the coating appearance can be improved. This has not been previously known.

The copolymer containing a structural unit derived from styrene and a structural unit derived from N-phenylmaleimide is commercially available, as, for example, Polyimilex (trade name) PSX0371, PAS1460, and PLM203 (all are manufactured by Nippon Shokubai Co., Ltd.), etc.

The content of the amorphous thermoplastic resin (C) in the resin composition of the present invention is not less than 1 part by weight and not more than 20 parts by weight with respect to 100 parts by weight of the matrix resin component in terms of improvement in thermal decomposition resistance and heat resistance. The lower limit of the content is preferably not less than 2 parts by weight, more preferably not less than 5 parts by weight, in terms of thermal decomposition resistance and heat resistance, and in terms of moldability and fluidity. The upper limit of the content is preferably not more than 15 parts by weight, more preferably not more than 10 parts by weight, in terms of prevention of a decrease in mechanical strength of a molded article and an increase in cost of a product. Specifically, when the content of the amorphous thermoplastic resin (C) is within the range of not less than 1 part by weight and not more than 20 parts by weight, the lower limit of the content range can be changed from not less than 1 part by weight to not less than 2 parts by weight or not less than 5 parts by weight, and the upper limit of the content range can be changed from not more than 20 parts by weight to not more than 15 parts by weight or not more than 10 parts by weight.

<Plate-Shaped Fillers (D)>

The plate-shaped fillers (D) according to the present invention (may also be hereinafter simply referred to as "the fillers") are, for example, a component that is used for the purpose, among purposes, of reducing the linear expansion of a molded article formed of the resin composition of the present invention, and include an alkaline inorganic material containing silica or alumina as a main component. The fillers are in the shape of a plate, a flake, a scale, etc., for example.

In the present invention, the plate-shaped fillers (D) need to have a number average major axis length of 0.1-45 μm. The number average major axis length is preferably 0.1-25 μm in terms of the low linear expansion and surface appearance of a molded article. The major axis length of the filler means the length of the longest straight line of the filler, i.e., the greatest length in a plane direction of the filler. The number average major axis length of the fillers is obtained by randomly selecting five fillers per field of view of a scanning electron microscope (SEM), measuring the major axis lengths of the selected fillers, performing this measurement for 20 fields of view, and calculating an arithmetic average of the obtained measured values. The number average aspect ratio of the fillers, i.e., the major axis length of the filler/the thickness of the filler, is preferably within the range of 2-200, more preferably 3-100, and even more preferably 3-75. The thickness of the filler means the greatest length of the lengths of straight lines perpendicular to the largest plane including the straight line that is the major axis of the filler, i.e., the greatest length in the thickness direction of the filler (a direction perpendicular to the largest plane including the straight line that is the major axis of the filler). The number average aspect ratio is obtained by additionally measuring the thicknesses of the fillers during the above measurement of the major axis lengths of the fillers, calculating the aspect ratios of the fillers, and calculating an arithmetic average of the obtained aspect ratios.

The content of the plate-shaped fillers (D) in the resin composition of the present invention is not less than 1 part by weight and not more than 50 parts by weight with respect to 100 parts by weight of the matrix resin component. The lower limit of the content is preferably not less than 3 parts by weight, more preferably not less than 5 parts by weight, in terms of low linear expansion and impact strength. The upper limit of the content is preferably not more than 40 parts by weight, more preferably not more than 35 parts by weight, in terms of the surface roughness and coating properties of a molded article. Specifically, when the content of the plate-shaped fillers (D) is within the range of not less than 1 part by weight and not more than 50 parts by weight, the lower limit of the content range may be changed from not less than 1 part by weight to not less than 3 parts by weight or not less than 5 parts by weight, and the upper limit of the content range may be changed from not more than 50 parts by weight to not more than 40 parts by weight or not more than 35 parts by weight.

The plate-shaped fillers (D) according to the present invention are not particularly limited as long as the filler contains silica or alumina as a main component and is plate-shaped. The plate-shaped filler (D) according to the present invention is preferably one or more selected from the group consisting of mica, talc, montmorillonite, sericite, kaolin, a glass flake, plate-shaped alumina, and synthetic hydrotalcite in terms of achievement of a dispersed state of each component in a molded article. Mica, talc, montmorillonite, sericite, kaolin, and a glass flake are more preferable in terms of improvement in the dimensional stability of the present invention. Mica, talc, a glass flake, and kaolin are more preferable, and mica, kaolin, and talc are particularly preferable, in terms of balance between impact resistance, fluidity, and product appearance.

The above mica may be either natural or synthetic, and may be any of muscovite, biotite, and phlogopite.

These plate-shaped fillers (D) may be used alone or in combination.

<Impact Modifier (E)>

The impact modifier (E) is preferably one or more selected from the group consisting of multistage graft polymers (E1), polyolefin polymers (E2), and olefin-unsaturated carboxylic acid ester copolymers and thermoplastic polyester elastomers (E3).

<Multistage Graft Polymer (E1)>

The multistage graft polymer (core type/shell type graft polymer) is obtained by graft polymerization of a vinyl compound onto a rubber-like elastic material.

The rubber-like elastic material is preferably one that has a glass transition temperature of not higher than 0° C., more preferably not higher than −40° C.

Specific examples of such a rubber-like elastic material include diene rubbers such as polybutadiene, butadiene-styrene copolymer, butadiene-acrylic acid ester copolymers, and butadiene-acrylonitrile copolymer, acrylic rubbers such as poly(butyl acrylate), poly(2-ethylhexyl acrylate), dimethylsiloxane-butyl acrylate rubber, and silicone/butyl acrylate composite rubber, olefin rubbers such as ethylene-propylene copolymer, and ethylene-propylene-diene copolymer, polydimethylsiloxane rubbers, and dimethylsiloxane-diphenylsiloxane copolymer rubbers.

Of them, acrylic rubbers are preferable, and polybutadiene, butadiene-styrene copolymer, butadiene-acrylic acid ester copolymers, etc., are more preferable in terms of impact resistance. Specific examples of the butadiene-acrylic acid ester copolymer rubbers include butadiene-butyl acrylate copolymer, and butadiene-2-ethylhexyl acrylate copolymer. Butadiene-butyl acrylate copolymer is more preferably used. Of the butadiene-butyl acrylate copolymer, copolymers of 50-70 wt % of butyl acrylate and 30-50 wt % of butadiene are preferable in terms of weather resistance and impact resistance.

The average particle size of the rubber-like elastic material is not particularly limited. The average particle size of the rubber-like elastic material is preferably within the range of 0.05-2.00 μm, more preferably 0.1-0.4 μm. The rubber-like elastic material may be one that contains an insoluble gel in a methylethylketone solvent. The gel content of the rubber-like elastic material is not particularly limited. The gel content of the rubber-like elastic material used is within the range of 10-99 wt %, or 70-98 wt %/o, and more preferably 80-96 wt %/o.

It is particularly preferable to use a multistage graft polymer that is produced by emulsion polymerization using an organic phosphorus emulsifier, for example. Examples of the organic phosphorus emulsifier include polyoxyethylene monoalkyl esters, polyoxyethylene dialkyl esters, polyoxyethylene trialkyl esters, etc., of phosphoric acid.

Examples of the vinyl compound that is subjected to graft polymerization onto the rubber-like elastic material in the above multistage graft polymer production include aromatic vinyl compounds, vinyl cyanide compounds, acrylic acid esters, methacrylic acid esters, etc. These may be used alone or in combination. Particularly preferable examples of the aromatic vinyl compound include styrene and α-methylstyrene. Particularly preferable examples of the vinyl cyanide compound include acrylonitrile and methacrylonitrile. Particularly preferable examples of the acrylic acid ester include methyl methacrylate.

The proportion between the rubber-like elastic material and the vinyl compound used in formulation of the multistage graft polymer is 10-90 wt %, more preferably 30-85 wt % of the rubber-like elastic material, and 90-10 wt %, more preferably 15-70 wt % of the vinyl compound. When the proportion of the rubber-like elastic material is less than 10 wt %, the effect of improving the impact resistance of the resin composition of the present invention is insufficient. Meanwhile, when the proportion of the rubber-like elastic material exceeds 90 wt %, the heat resistance of the resin composition of the present invention tends to decrease.

<Polyolefin Polymer (E2)>

Examples of the polyolefin polymer (E2) include, but are not limited to, polyethylene, polypropylene, etc., which can be suitably used. The polyolefin polymer may be either homopolymers, or copolymers such as ethylene-propylene copolymer, ethylene-butene copolymer, ethylene-4-methylpentene copolymer, ethylene-hexene copolymer, ethylene-octene copolymer, and propylene-butene copolymer. The degree of polymerization of the polyolefin polymer is not particularly limited. Typically, any polyolefin polymer that has a melt index within the range of 0.05-50 g/10 min may be selected and used. Of such polyolefin polymers, ethylene-butene copolymer, ethylene-hexene copolymer, and ethylene-octene copolymer are preferable in terms of further improvement in impact resistance.

<One or More Selected from Group Consisting of Olefin-Unsaturated Carboxylic Acid Ester Copolymers and Thermoplastic Polyester Elastomers (E3)>

Examples of olefins in the olefin-unsaturated carboxylic acid ester copolymers (E3) include ethylene, propylene, 1-butene, 1-pentene, 1-hexene, 1-octene, etc. These olefins may be used alone or in combination. Ethylene is particularly preferable as such an olefin.

Examples of unsaturated carboxylic acid esters in the olefin-unsaturated carboxylic acid esters include methyl acrylate, ethyl acrylate, n-propyl acrylate, i-propyl acrylate, n-butyl acrylate, t-butyl acrylate, 2-ethylhexyl acrylate, glycidyl acrylate, methyl methacrylate, ethyl methacrylate, n-propyl methacrylate, i-propyl methacrylate, n-butyl methacrylate, t-butyl methacrylate, 2-ethylhexyl methacrylate, glycidyl methacrylate, etc. These may be used alone or in combination. Methyl acrylate, ethyl acrylate, and glycidyl methacrylate are particularly preferable as such an alkyl (meth)acrylate ester.

The copolymerization ratio by weight of the olefin unit and the unsaturated carboxylic acid ester unit (olefin/unsaturated carboxylic acid ester) in the olefin-unsaturated carboxylic acid ester copolymer is preferably 40160-95/5, more preferably 50/50-90/10. When the copolymerization ratio of the unsaturated carboxylic acid ester unit in the copolymer is less than 5, the chemical resistance improving effect is insufficient in many cases. When the copolymerization ratio of the unsaturated carboxylic acid ester unit in the copolymer exceeds 60, the thermal stability during melting (e.g., during a molding process) is insufficient in many cases.

Examples of the olefin-unsaturated carboxylic acid ester copolymer include ethylene-methyl acrylate copolymer, ethylene-ethyl acrylate copolymer, ethylene-propyl acrylate copolymer, ethylene-butyl acrylate copolymer, ethylene-hexyl acrylate copolymer, ethylene-2-ethylhexyl acrylate copolymer, ethylene-methyl methacrylate copolymer, ethylene-butyl methacrylate copolymer, ethylene-hexyl methacrylate copolymer, ethylene-2-ethylhexyl methacrylate copolymer, ethylene-glycidyl acrylate copolymer, ethylene-glycidyl methacrylate copolymer, ethylene-glycidyl acrylate-vinyl acetate copolymer, ethylene-glycidyl methacrylate-vinyl acetate copolymer, ethylene-glycidyl acrylate-methyl acrylate copolymer, ethylene-glycidyl methacrylate-methyl acrylate copolymer, etc. Of them, ethylene-ethyl acrylate copolymer, ethylene-glycidyl methacrylate copolymer, ethylene-glycidyl methacrylate-vinyl acetate copolymer, and ethylene-glycidyl methacrylate-methyl acrylate copolymer are preferable in terms of further improvement in impact resistance. Vinyl acetate, styrene, etc., can be further copolymerized into the olefin-unsaturated carboxylic acid ester copolymer.

The thermoplastic polyester elastomer refers to a copolymer containing an aromatic dicarboxylic acid or an ester-formable derivative thereof, a diol or an ester-formable derivative thereof, and a polyether having a number average molecular weight of 700-3000. The proportion of the component derived from the polyether is preferably within the range of 5-80 wt %, more preferably 10-70 wt %. When the proportion of the component derived from the polyester is less than 5 wt %, the effect of improving the impact resistance of the resin composition of the present invention tends to be insufficient. When the proportion of the component derived from the polyester exceeds 80 wt %, the heat resistance of the resin composition of the present invention is likely to decrease.

The solution viscosity of the thermoplastic polyester elastomer in a mixture solvent of phenol and tetrachloroethane at (a weight ratio of) 1/1 is such that the logarithmic viscosity (IV) is preferably within the range of 0.3-2.0 dl/g at 25° C. and a concentration of 0.5 g/dl (5 g/l), more preferably 0.4-1.5 dl/g. When the logarithmic viscosity is less than 0.3 dl/g, the impact resistance, the chemical resistance, etc., are likely to decrease. Meanwhile, when the logarithmic viscosity exceeds 2.0 dl/g, the moldability, etc., tend to decrease.

Specific examples of the aromatic dicarboxylic acid or an ester-formable derivative thereof for use in production of the thermoplastic polyester elastomer include terephthalic acid, isophthalic acid, and ester-formable derivatives thereof, etc. These may be used alone or in combination. Meanwhile, examples of the diol or an ester-formable derivative thereof include ethylene glycol, propylene glycol, tetramethylene glycol, and ester-formable derivatives thereof, etc. These may be used alone or in combination. Examples of the polyether include polyethylene glycol, polypropylene glycol, polytetramethylene glycol, copolymers of ethylene oxide and propylene oxide, etc. These may be used alone or in combination. The number average molecular weight of the polyether is preferably within the range of 700-3000. When the number average molecular weight is less than 700, the heat resistance tends to decrease. Meanwhile, when the number average molecular weight exceeds 3000, the thermal stability tends to decrease.

<Stabilizer>

The resin composition of the present invention may contain a stabilizer as an optional component as long as the effects of the resin composition are not impaired. The stabilizer is preferably one or more selected from the group consisting of phenol stabilizers, phosphorus stabilizers, and sulfur stabilizers. Because of their excellent thermal stability, these stabilizers are more preferably used in combination.

The phosphorus stabilizer is more preferably a phosphite stabilizer, including, but not limited to, tris(2,4-di-t-butyl-phenyl)phosphite (e.g., ADKSTAB (registered trademark) 2112, manufactured by Asahi Denka Kabushiki Kaisha), etc.

The phenol stabilizer is more preferably a hindered phenol stabilizer, including, but not limited to, pentaerythritol tetrakis[3-(3,5-di-t-butyl-4-hydroxyphenyl)propionate (e.g., IRGANOX (registered trademark) 1010, manufactured by Ciba Specialty Chemicals), etc.

<Other Additives>

The resin composition of the present invention may contain a commonly used resin additive as long as the preferable characteristics and effects of the composition are not impaired. Examples of the resin additive include photostabilizers, flame retardants, plasticizers, lubricants, release agents, UV absorbers, antistatic agents, pigments and dyes, inorganic fillers other than the plate-shaped fillers (D), resin components, such as acrylonitrile-styrene copolymers, etc., other than the resins (A)-(C), etc. These resin additives may be used alone or in combination.

<Production Method>

The resin composition of the present invention may be produced in any method. For example, the resin composition of the present invention is produced by mixture using a blender super mixer, etc., or kneading using a single- or multiple-screw extruder, etc.

<Molding Method>

The resin composition of the present invention may be molded in any method. For example, the resin composition of the present invention may be molded using injection molding, extrusion molding, blow molding, compression molding, etc.

<Molded Article>

The resin composition of the present invention is an excellent material for large-sized molded articles. More specifically, the large-sized molded article refers to a molded article having length and width dimensions of about 300-4000 mm×100-2500 mm, and a maximum projected area of 10,000 mm$^2$-10,000,000 mm$^2$. The maximum projected area of the molded article is preferably 30,000 mm$^2$-7,000,000 mm$^2$, more preferably 50,000 mm$^2$-4,000,000 mm$^2$. The linear expansion coefficient of the large-sized molded article is preferably $6.5 \times 10^{-5}/°$ C.-$3.5 \times 10^{-5}/°$ C., as measured as an in-plane linear expansion coefficient at a measurement temperature between $-30°$ C. and $+80°$ C. More specifically, a molded article having a maximum projected area over 30000 mm$^2$, and an in-plane linear expansion coefficient of not more than $6.5 \times 10^{-5}/°$ C. at a measurement temperature between $-30°$ C. and $+80°$ C., is preferable.

The projected area refers to the area of the shadow of a molded article as illuminated with parallel light. When the projected area of a molded article varies depending on its shape and the direction of a light source, the maximum projected area is determined as the greatest value of the projected areas obtained when the molded article is rotated around all of the three-dimensional axes (X-axis, Y-axis, and Z-axis).

The molded article of the present invention having such characteristics can be advantageously used for, for example, parts for vehicles, etc. Of parts for vehicles, the molded article of the present invention can be advantageously used for automotive exterior parts, particularly garnishes, pillars, and spoilers. Of the automotive exterior parts, the heat resistance and thermal decomposition resistance of the resin composition of the present invention are most advantageously exhibited in automotive horizontal exterior members. Of the horizontal exterior members, rear spoilers, hoods (covers), roof panels, roof side garnishes, and tailgate garnishes are more preferable.

<Applications>

The resin composition of the present invention is molded into automotive parts, electric and electronic components, sundry goods, etc., using various known techniques such as injection molding and extrusion molding. The resulting molded articles have excellent heat resistance, impact resistance, rigidity, dimensional stability, chemical resistance, moldability, weather resistance, and thermal stability (thermal decomposition resistance), and also excellent surface gloss and appearance.

EXAMPLES

The polycarbonate resin composition of the present invention will now be specifically described on the basis of examples.

In the following measurement conditions, examples, etc., the terms "part(s)" and "%" refer to "part(s) by weight" and "wt %", respectively.

<Blended Materials>

Firstly, materials used and measurement conditions will now be described.

[Polycarbonate Resin (A)]

(A-1) Product name: TARFLON (registered trademark) A2200, having a viscosity average molecular weight of 22,000, manufactured by Idemitsu Kosan Co., Ltd.

(A-2) Product name: Lupilon (registered trademark) H3000, having a viscosity average molecular weight of 17,000, manufactured by Mitsubishi Engineering-Plastics Corporation

[Thermoplastic Polyester Resin (B)]

(B-1) Polyethylene terephthalate resin having a logarithmic viscosity of 0.75 dl/g, product name: EFG-70, manufactured by Bell Polyester Products, Inc.

[Amorphous Thermoplastic Resin (C)]

(C-1) Polyphenylene ether resin, product name: Lupiace (registered trademark) PX-100L, having a glass transition temperature of 219° C. and an intrinsic viscosity of 0.47 dl/g, manufactured by Mitsubishi Engineering-Plastics Corporation (C-2) Polyarylate resin, product name: U polymer (registered trademark) U-100, having a glass transition temperature of 195° C., manufactured by Unitika Ltd.

(C-3) Polyetherimide resin having a glass transition temperature of 220° C., product name: ULTEM (registered trademark) 1000, SABIC Innovative Plastics (C-4) N-phenylmaleimide-styrene copolymer, product name: Polyimilex (registered trademark) PSX0371, having a glass transition temperature of 199° C., manufactured by Nippon Shokubai Co., Ltd., which is hereinafter referred to as "the modified styrene resin 1"

(C-5) N-phenylmaleimide-acrylonitrile-styrene copolymer, product name: Polyimilex (registered trademark) PAS1460, having a glass transition temperature of 169° C., manufactured by Nippon Shokubai Co., Ltd., which is hereinafter referred to as "the modified styrene resin 2"

(C-6) Polystyrene resin, product name: Toyo Styrol GP (registered trademark) HRM24N, having a glass transition temperature of 103° C., manufactured by Toyo Styrene Co., Ltd.

[Plate-Shaped Filler (D)]

(D-1) Mica, product name: Muscovite Mica A-21S, having a number average major axis length of 27 μm and a number average aspect ratio of 70, manufactured by Yamaguchi Mica Co., Ltd.

(D-2) Mica, product name: Muscovite Mica A-41S, having a number average major axis length of 40 μm and a number average aspect ratio of 80, manufactured by Yamaguchi Mica Co., Ltd.

(D-3) Talc, product name: Rose Talc, having a number average major axis length of 17 μm and a number average aspect ratio of 24, manufactured by Nippon Talc Co., Ltd.

(D-4) Mica, product name: Mica W-20, having a number average major axis length of 5 μm and a number average aspect ratio of 20, manufactured by Lingshou Huajing Mica Co., Ltd.

(D-5) Kaolin, product name: Translink 77, having a number average major axis length of 0.7 μm and a number average aspect ratio of 12, manufactured by BASF Japan Ltd.

<Evaluation Method>

Next, an evaluation method will now be described.

(Heat Resistance)

As an index of heat resistance, a deflection temperature under load (° C.) was measured under a load of 1.80 MPa according to ISO 75.

(Thermal Deformation Resistance)

As an index of thermal deformation resistance, a heat sag test was conducted using a test piece according to JIS K7195. The quantity of thermal deformation was measured after 5 hours in a hot air oven at 100° C. The quantity of thermal deformation refers to a height from the horizontal plane to a position of longitudinal one end of the test piece placed on the horizontal plane, when the other end of the test piece is pressed and held. The quantity of thermal deformation was measured using calipers.

(Thermal Decomposition Resistance)

Pellets of the obtained polycarbonate resin composition were dried at 130° C. for 4 hours. Thereafter, the pellets were heated so that the temperature thereof was increased from room temperature to 500° C. at a rate of 10° C./min, and the temperature at which the degree (%) of a reduction in weight from the initial weight was 1%, and the weight reduction start temperature in the case of one-step weight reduction according to JIS K7120, were measured using a differential thermal/thermogravimetric simultaneous measurement device (TG/DTA7200, manufactured by Hitachi High-Tech Science Corporation). As the 1% weight reduction temperature and the weight reduction start temperature increase, the decomposition gas is less likely to occur, and the defective appearance of a molded article is less likely to occur.

(Fluidity)

As an index of fluidity, a spiral flow was measured. Pellets of the obtained polycarbonate resin composition were dried at 130° C. for 4 hours. Thereafter, the pellets were molded using an injection molding machine (product name: FAS-150, manufactured by Fanuc Corporation) at a cylinder temperature of 280° C., a die temperature of 80° C., and an injection pressure of 1000 kg/cm². A spiral flow (mm) was measured in a spiral molded article (width of 10 mm y thickness of 2 mm, pitch: 5 mm).

(Molded Article Moldability)

As an index of moldability, surface properties of a large-sized molded article molded using the polycarbonate resin composition were evaluated. Pellets of the obtained polycarbonate resin composition were dried at 130° C. for 4 hours. Thereafter, automotive panel parts that are three large-sized injection molded articles having thicknesses of 3.0 mm, 2.5 mm, and 2.0 mm, respectively, and a maximum projected area of 600 mm×200 mm (the distance between the gate and an end is 600 mm) were produced as test pieces using an injection molding machine (product name: 850-MG160, manufactured by Mitsubishi Heavy Industries, Ltd.) at a cylinder temperature of 280° C. The test pieces were observed by the naked eyes and evaluated according to the following criteria. When the injection molding die is filled with a resin composition even up to peripheral portions thereof, and even automotive panel parts, having a smaller thickness, which are made of the resin composition have better surface appearance, the resin composition can be said to have more excellent large-size moldability.

[Criteria for Evaluation of Surface Properties]

⊚: The injection molding die was filled with the resin composition up to peripheral portions thereof, and no flash was observed on the surface, and the surface had dense and good texture, and was glossy.

○: The injection molding die was filled with the resin composition up to peripheral portions thereof, and substantially no flash was observed on the surface, and the surface had dense and good texture.

Δ: The injection molding die was filled with the resin composition up to peripheral portions thereof, and flash was slightly observed on the surface, and the surface was slightly poor in dense texture.

x: The injection molding die was filled with the resin composition up to peripheral portions thereof, but flash was significantly observed on the surface, and the surface had poor texture.

xx: The injection molding die was not filled with the resin composition up to the peripheral portions thereof.

(Surface Roughness of Molded Article)

Surface roughnesses of molded articles, obtained using the above method, each of which had a dimension of 600 mm×200 mm, and which had thicknesses of 3.0 mm, 2.5 mm, and 2.0 mm, respectively, were measured using a laser microscope as an index of surface roughness. An average roughness Ra (μm) was calculated at a measurement length of 800 μm (cut-off value: 0.8 μm).

(Coating Properties of Molded Article)

A coating was applied to molded articles, obtained using the above method, each of which had a dimension of 600 mm×200 mm, and which had thicknesses of 3.0 mm, 2.5 mm, and 2.0 mm, respectively, and evaluation was made according to the following criteria. When the coating film was removed at a ratio of greater than 5/100 in a cross-cut test, it was determined the adhesion of the coating film was insufficient. As to surface appearance, i.e., image clearness that was evaluated when a character was reflected on the coated surface like a mirror, when the character was not clearly read as observed at a distance of 40 cm, it was determined that the appearance was insufficient.

[Criteria for Evaluation of Coating Properties of Molded Article]

○: A coating film surface had good surface appearance, and had no problem with coating film adhesion. The coated surface had specular gloss, and clear reflections of the contours of a character, a face of a person, and an object, which were therefore clearly distinguishable, were observed.

Δ: A coating film surface had non-uniform and poor surface appearance, and had no problem with coating film adhesion. The coated surface had specular gloss, but slightly unclear reflections of the contours of a character, a face of a person, and an object, which were therefore difficult to distinguish in some cases, were observed.

x: A coating film surface had non-uniform and poor surface appearance, and had insufficient coating film adhesion. The coated surface had poor gloss, and unclear reflections of the contours of a character, a face of a person, and an object, which were therefore difficult to distinguish in most cases, were observed.

(Low Linear Expansion)

As an index of low linear expansion, a linear expansion coefficient was evaluated. A test piece obtained by cutting a middle portion out of a molded article according to JIS K7197 was tested for evaluation of linear expansion coefficients in a flow (MD) direction and a perpendicular (TD) direction to the flow at measurement temperatures between −30° C. and +80° C.

Examples 1-22 and Comparative Examples 1-4

Dry blending was previously performed according to materials and blending composition (unit: part by weight) shown in Tables 1 and 2. The dry blend was supplied through a hopper hole to a vent co-rotation twin-screw extruder having a diameter of 44 mm (product name: TEX44, manufactured by The Japan Steel Works, Ltd.) and subjected to melt-kneading at a cylinder temperature setting of 250-280° C., followed by pelletizing. Thus, the resin composition in the form of pellets was prepared. The resin composition thus obtained was evaluated using the above evaluation method. The results of evaluation are shown in Tables 1 and 2.

In Tables 1 and 2, the thermoplastic polyester resin (B) is denoted by "PE resin (B)", the polyethylene terephthalate resin is denoted by "PET resin", and the polyphenylene ether resin is denoted by "PPE resin."

As can be seen from Tables 1 and 2, the resin composition of the present invention has excellent thermal decomposition resistance. Thus, a resin composition can be provided which does not impair the appearance of even a large-sized molded article, and has a good balance between heat resistance, moldability, and low linear expansion.

TABLE 1

| | | | | Examples | | | | | | |
|---|---|---|---|---|---|---|---|---|---|---|
| | | | | 1 | 2 | 3 | 4 | 5 | 6 | 7 |
| Blending composition | (A) PC resin | (A-1) | Polycarbonate resin | 70 | 75 | 36 | 60 | | 85 | |
| | | (A-2) | Polycarbonate resin | | | 36 | | 74 | | 74 |
| | (B) PE resin | (B-1) | PET resin | 30 | 25 | 28 | 40 | 26 | 15 | 26 |
| | (C) Amorphous thermoplastic resin | (C-1) | PPE resin | 1 | 5 | 6 | 5 | 5 | 15 | 5 |
| | | (C-2) | Polyarylate resin | | | | | | | |
| | | (C-3) | Polyetherimide resin | | | | | | | |
| | | (C-4) | Modified styrene resin 1 | | | | | | | |
| | | (C-5) | Modified styrene resin 2 | | | | | | | |
| | | (C-6) | Polystyrene | | | | | | | |
| | (D) Plate-shaped fillers | (D-1) | Mica number average major axis length 27 μm | 10 | 10 | 11 | 10 | 11 | 10 | |
| | | (D-2) | Mica number average major axis length 40 μm | | | | | | | |
| | | (D-3) | Talc number average major axis length 17 μm | | | | | | | 11 |
| | | (D-4) | Mica number average majo raxis length 5 μm | | | | | | | |
| | | (D-5) | Kaolin number average major axis length 0.7 μm | | | | | | | |
| Evaluation | Fluidity | | Spiral flow (2 mm thick, mm) | 330 | 320 | 350 | 345 | 380 | 300 | 370 |
| | Heat resistance | | Deflection temperature under load (1.80 MPa, ° C.) | 114 | 113 | 113 | 114 | 113 | 114 | 113 |
| | | | Heat sag (100° C. × 5 h, mm) | 1.00 | 0.25 | 0.25 | 0.25 | 0.25 | 0.00 | 0.25 |
| | Thermal decomposition resistance | | 1% weight reduction temperature (° C.) | 375 | 375 | 377 | 375 | 375 | 375 | 374 |
| | | | Weight reduction start temperature (° C.) | 413 | 414 | 413 | 413 | 414 | 413 | 412 |
| | Moldability | Large-sized molded article Surface properties | (3.0 mm-thick panel part) | ◎ | ◎ | ◎ | ◎ | ◎ | ◎ | ◎ |
| | | | (2.5 mm-thick panel part) | ◎ | ◎ | ◎ | ◎ | ◎ | ○ | ◎ |
| | | | (2.0 mm-thick panel part) | ○ | ○ | ◎ | ○ | ◎ | ○ | ○ |
| | Surface properties | Large-sized molded article Surface roughness (μm) | (3.0 mm-thick panel part, μm) | 2.2 | 2.3 | 2.5 | 2.2 | 2.5 | 2.5 | 2.0 |
| | | | (2.5 mm-thick panel part, μm) | 2.3 | 2.3 | 2.5 | 2.2 | 2.5 | 2.8 | 2.1 |
| | | | (2.0 mm-thick panel part, μm) | 2.3 | 2.5 | 2.5 | 2.1 | 2.5 | 3.3 | 2.1 |
| | Coating properties | Large-sized molded article Coating appearance | (3.0 mm-thick panel part) | ○ | ○ | ○ | ○ | ○ | ○ | ○ |
| | | | (2.5 mm-thick panel part) | ○ | ○ | ○ | ○ | ○ | Δ | ○ |
| | | | (2.0 mm-thick panel part) | ○ | ○ | ○ | ○ | ○ | Δ | ○ |
| | Linear expansion | | Linear expansion coefficient in MD direction | 5.0 | 5.1 | 5.0 | 5.2 | 5.0 | 5.1 | 4.9 |
| | | | Linear expansion coefficient in TD direction | 5.2 | 5.2 | 5.2 | 5.3 | 5.2 | 5.3 | 5.1 |

TABLE 1-continued

| | | | | Examples | | | | | | |
|---|---|---|---|---|---|---|---|---|---|---|
| | | | | 8 | 9 | 10 | 11 | 12 | 13 | 14 |
| Blending composition | (A) PC resin | (A-1) | Polycarbonate resin | 70 | | | | | | |
| | | (A-2) | Polycarbonate resin | | 75 | 75 | 75 | 75 | 75 | 75 |
| | (B) PE resin | (B-1) | PET resin | 30 | 25 | 25 | 25 | 25 | 25 | 25 |
| | (C) Amorphous thermoplastic resin | (C-1) | PPE resin | 5 | 5 | 5 | 5 | 10 | 5 | |
| | | (C-2) | Polyarylate resin | | | | | | | 5 |
| | | (C-3) | Polyetherimide resin | | | | | | | |
| | | (C-4) | Modified styrene resin 1 | | | | | | | |
| | | (C-5) | Modified styrene resin 2 | | | | | | | |
| | | (C-6) | Polystyrene | | | | | | | |
| | (D) Plate-shaped fillers | (D-1) | Mica number average major axis length 27 µm | | 20 | 5 | 3 | 10 | 10 | 10 |
| | | (D-2) | Mica number average major axis length 40 µm | 10 | | | | | | |
| | | (D-3) | Talc number average major axis length 17 µm | | | | | | | |
| | | (D-4) | Mica number average majo raxis length 5 µm | | | | | | | |
| | | (D-5) | Kaolin number average major axis length 0.7 µm | | | | | | | |
| Evaluation | Fluidity | Spiral flow (2 mm thick, mm) | | 325 | 400 | 370 | 375 | 355 | 390 | 330 |
| | Heat resistance | Deflection temperature under load (1.80 MPa, ° C.) | | 114 | 114 | 114 | 113 | 114 | 114 | 113 |
| | | Heat sag (100° C. × 5 h, mm) | | 0.25 | 0.25 | 0.75 | 0.75 | 0.25 | 0.25 | 1.00 |
| | Thermal decomposition resistance | 1% weight reduction temperature (° C.) | | 374 | 375 | 375 | 374 | 375 | 375 | 374 |
| | | Weight reduction start temperature (° C.) | | 414 | 413 | 412 | 413 | 413 | 414 | 413 |
| | Moldability | Large-sized molded article Surface properties | (3.0 mm-thick panel part) | ◉ | ◉ | ◉ | ◉ | ◉ | ◉ | ◉ |
| | | | (2.5 mm-thick panel part) | ○ | ◉ | ◉ | ◉ | ◉ | ◉ | ○ |
| | | | (2.0 mm-thick panel part) | Δ | ○ | ◉ | ○ | ◉ | ◉ | ○ |
| | Surface properties | Large-sized molded article Surface roughness (µm) | (3.0 mm-thick panel part, µm) | 3.2 | 2.5 | 2.3 | 2.3 | 2.5 | 2.5 | 2.9 |
| | | | (2.5 mm-thick panel part, µm) | 3.2 | 2.6 | 2.3 | 2.3 | 2.5 | 2.5 | 2.9 |
| | | | (2.0 mm-thick panel part, µm) | 3.6 | 2.7 | 2.3 | 2.4 | 2.6 | 2.5 | 2.9 |
| | Coating properties | Large-sized molded article Coating appearance | (3.0 mm-thick panel part) | Δ | ○ | ○ | ○ | ○ | ○ | Δ |
| | | | (2.5 mm-thick panel part) | Δ | ○ | ○ | ○ | ○ | ○ | Δ |
| | | | (2.0 mm-thick panel part) | Δ | ○ | ○ | ○ | ○ | ○ | Δ |
| | Linear expansion | Linear expansion coefficient in MD direction | | 4.9 | 4.2 | 5.4 | 6.1 | 5.0 | 5.1 | 5.2 |
| | | Linear expansion coefficient in TD direction | | 5.0 | 4.4 | 5.5 | 6.3 | 5.1 | 5.3 | 5.3 |

TABLE 2

| | | | | Examples | | | | | |
|---|---|---|---|---|---|---|---|---|---|
| | | | | 15 | 16 | 17 | 18 | 19 | 20 |
| Blending composition | (A) PC resin | (A-1) | Polycarbonate resin | | | | | | |
| | | (A-2) | Polycarbonate resin | 75 | 75 | 75 | 75 | 75 | 75 |
| | (B) PE resin | (B-1) | PET resin | 25 | 25 | 25 | 25 | 25 | 25 |
| | (C) Amorphous thermoplastic resin | (C-1) | PPE resin | | | | | | 5 |
| | | (C-2) | Polyarylate resin | | | | | | |
| | | (C-3) | Polyetherimide resin | 5 | | | | | |
| | | (C-4) | Modified styrene resin 1 | | 5 | | 5 | | |
| | | (C-5) | Modified styrene resin 2 | | | 5 | | 5 | |
| | | (C-6) | Polystyrene | | | | | | |
| | (D) Plate-shaped fillers | (D-1) | Mica number average major axis length 27 µm | 10 | 10 | 10 | | | |
| | | (D-2) | Mica number average major axis length 40 µm | | | | | | |
| | | (D-3) | Talc number average major axis length 17 µm | | | | | | |
| | | (D-4) | Mica number average major axis length 5 µm | | | | 20 | | 10 |
| | | (D-5) | Kaolin number average major axis length 0.7 µm | | | | | 30 | |

TABLE 2-continued

| Evaluation | | | | | | | | |
|---|---|---|---|---|---|---|---|---|
| Fluidity | | Spiral flow (2 mm thick, mm) | 300 | 395 | 390 | 410 | 405 | 380 |
| Heat resistance | | Deflection temperature under load (1.80 MPa, °C.) | 111 | 114 | 113 | 114 | 114 | 112 |
| | | Heat sag (100° C. × 5 h, mm) | 0.50 | 0.25 | 0.25 | 0.25 | 0.25 | 0.25 |
| Thermal decomposition resistance | | 1% weight reduction temperature (°C.) | 375 | 375 | 374 | 375 | 375 | 374 |
| | | Weight reduction start temperature (°C.) | 420 | 412 | 411 | 414 | 413 | 413 |
| Moldability | Large-sized molded article | (3.0 mm-thick panel part) | ○ | ◎ | ◎ | ◎ | ◎ | ◎ |
| | | (2.5 mm-thick panel part) | ○ | ◎ | ◎ | ◎ | ◎ | ◎ |
| | Surface properties | (2.0 mm-thick panel part) | ○ | ◎ | ◎ | ◎ | ◎ | ◎ |
| Surface properties | Large-sized molded article | (3.0 mm-thick panel part) | 3.2 | 2.0 | 2.1 | 2.1 | 2.1 | 2.1 |
| | | (2.5 mm-thick panel part) | 3.2 | 2.0 | 2.1 | 2.1 | 2.1 | 2.1 |
| | Surface roughness (μm) | (2.0 mm-thick panel part) | 3.2 | 2.0 | 2.1 | 2.2 | 2.2 | 2.1 |
| Coating properties | Large-sized molded article | (3.0 mm-thick panel part) | Δ | ○ | ○ | ○ | ○ | ○ |
| | | (2.5 mm-thick panel part) | Δ | ○ | ○ | ○ | ○ | ○ |
| | Coating appearance | (2.0 mm-thick panel part) | Δ | ○ | ○ | ○ | ○ | ○ |
| Linear expansion | | Linear expansion coefficient in MD direction | 5.0 | 4.9 | 5.2 | 4.5 | 5.2 | 5.1 |
| | | Linear expansion coefficient in TD direction | 5.2 | 5.1 | 5.3 | 4.7 | 5.3 | 5.2 |

| | | | | Examples | | Comparative Examples | | | |
|---|---|---|---|---|---|---|---|---|---|
| | | | | 21 | 22 | 1 | 2 | 3 | 4 |
| Blending composition | (A) PC resin | (A-1) | Polycarbonate resin | | | 70 | 70 | | 70 |
| | | (A-2) | Polycarbonate resin | 75 | 75 | | | 75 | |
| | (B) PE resin | (B-1) | PET resin | 25 | 25 | 30 | 25 | 25 | 30 |
| | (C) Amorphous thermoplastic resin | (C-1) | PPE resin | 5 | 5 | | 25 | | |
| | | (C-2) | Polyarylate resin | | | | | | |
| | | (C-3) | Polyetherimide resin | | | | | | |
| | | (C-4) | Modified styrene resin 1 | | | | | | |
| | | (C-5) | Modified styrene resin 2 | | | | | | |
| | | (C-6) | Polystyrene | | | | | 5 | |
| | (D) Plate-shaped fillers | (D-1) | Mica number average major axis length 27 μm | | | 10 | 10 | 10 | 19 |
| | | (D-2) | Mica number average major axis length 40 μm | | | | | | |
| | | (D-3) | Talc number average major axis length 17 μm | | | | | | |
| | | (D-4) | Mica number average major axis length 5 μm | | | | | | |
| | | (D-5) | Kaolin number average major axis length 0.7 μm | 10 | 30 | | | | |
| Evaluation | Fluidity | | Spiral flow (2 mm thick, mm) | 390 | 395 | 330 | 190 | 340 | 335 |
| | Heat resistance | | Deflection temperature under load (1.80 MPa, °C.) | 111 | 112 | 109 | 133 | 109 | 109 |
| | | | Heat sag (100° C. × 5 h, mm) | 0.25 | 0.25 | 1.00 | 0.00 | 1.00 | 0.75 |
| | Thermal decomposition resistance | | 1% weight reduction temperature (°C.) | 375 | 375 | 372 | 378 | 370 | 370 |
| | | | Weight reduction start temperature (°C.) | 413 | 414 | 409 | 432 | 408 | 408 |
| | Moldability | Large-sized molded article | (3.0 mm-thick panel part) | ◎ | ◎ | Δ | XX | ○ | Δ |
| | | | (2.5 mm-thick panel part) | ◎ | ◎ | X | XX | Δ | X |
| | | Surface properties | (2.0 mm-thick panel part) | ◎ | ◎ | X | XX | X | X |
| | Surface properties | Large-sized molded article | (3.0 mm-thick panel part) | 1.9 | 2.4 | 1.8 | — | 2.1 | 2.1 |
| | | | (2.5 mm-thick panel part) | 2.0 | 2.4 | 1.8 | — | 2.1 | 2.1 |
| | | Surface roughness (μm) | (2.0 mm-thick panel part) | 2.0 | 2.4 | 1.8 | — | 2.1 | 2.2 |
| | Coating properties | Large-sized molded article | (3.0 mm-thick panel part) | ○ | ○ | ○ | — | ○ | ○ |
| | | | (2.5 mm-thick panel part) | ○ | ○ | ○ | — | ○ | ○ |
| | | Coating appearance | (2.0 mm-thick panel part) | ○ | ○ | ○ | — | ○ | ○ |
| | Linear expansion | | Linear expansion coefficient in MD direction | 5.8 | 5.3 | 5.1 | 5.1 | 5.3 | 4.3 |
| | | | Linear expansion coefficient in TD direction | 5.9 | 5.4 | 5.2 | 5.3 | 5.4 | 4.5 |

Figure 3:
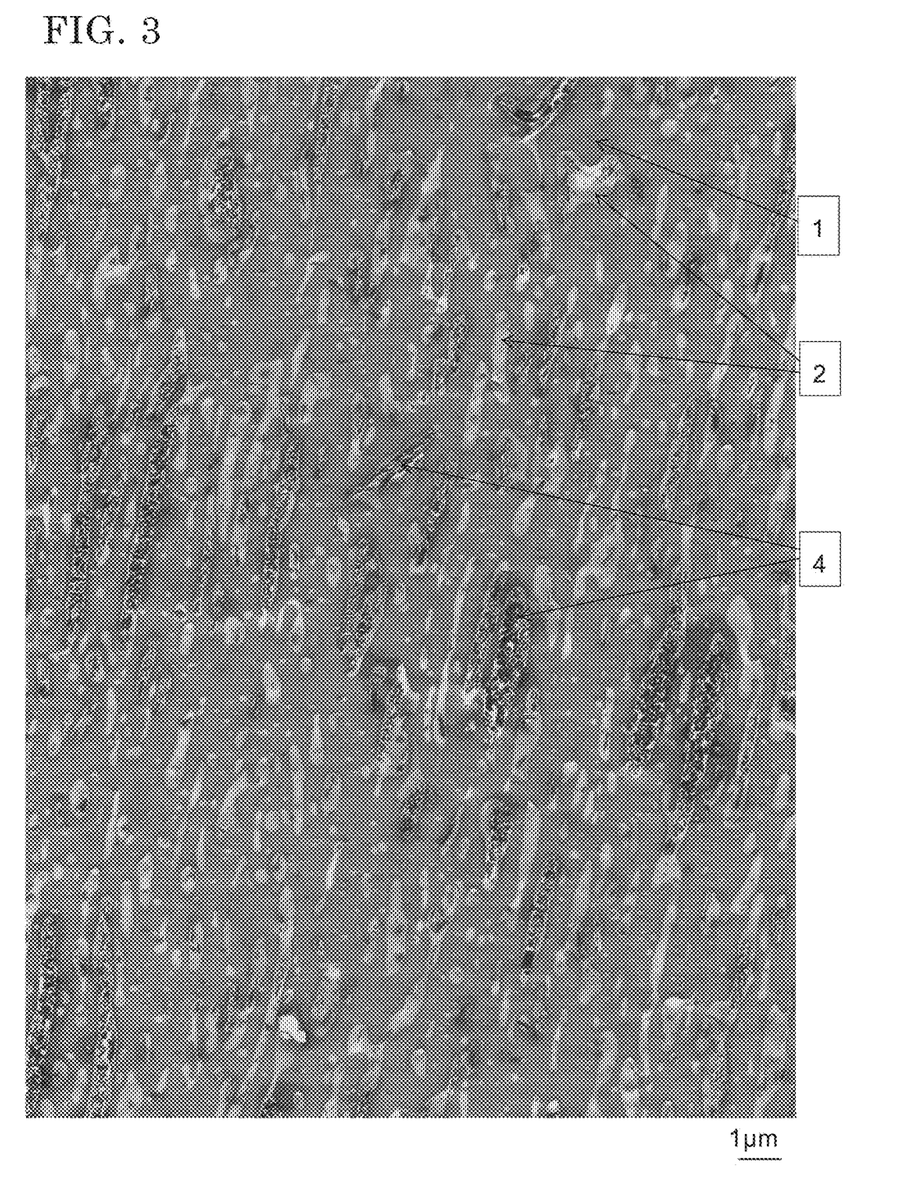
FIG. 3 is a transmission electron microscope photograph of a pellet of a resin composition obtained in Comparative Example 4.

In FIGS. 1-3, the dark gray portion 1 indicates the polycarbonate resin (sea), and the light gray portions (islands) 2 are dispersed in the gray polycarbonate resin (sea). The light gray portions (islands) 2 indicate the polyethylene terephthalate resin, and some of the light gray portions (islands) 2 cover the entirety of the black portion 4 that is an aggregate of plate-shaped fillers. In FIGS. 1 and 2, the light gray portions (islands) 3 that are different from the light gray portions (islands) 2 are independently dispersed in the polycarbonate resin (sea) without covering the black portions 4. The gray portions (islands) 3 indicate the polyphenylene ether resin. The gray portion 3 may contain plate-shaped fillers that are not in the form of the black portion 4.

In the electron microscope photograph of the pellet of Example 2 shown in FIG. 1, a sea/island/island structure is formed in which the polyethylene terephthalate resin and the polyphenylene ether resin are both dispersed as islands in the sea of the polycarbonate resin. The polyethylene terephthalate resin, which has a low melt viscosity, is elongated and stretched in a shear field in the polycarbonate resin, and surrounds plate-shaped fillers. The melt viscosity of the polyphenylene ether resin, which has a high glass transition temperature, increases earliest during cooling from the melt state, and therefore, is dispersed in the polycarbonate resin, in the shape of a nearly perfect circle having a maximum diameter of less than about 3 μm, without surrounding plate-shaped fillers. Thus, it is considered that the polyphenylene ether resin is dispersed as islands in the polycarbonate resin, and therefore, the polyphenylene ether resin functions like organic fillers to provide the effect of increasing the heat resistance, and at the same time, the fine dispersion of the polyphenylene ether resin results in a good balance between heat resistance and fluidity, without having a significant influence on fluidity.

In the electron microscope photograph of the pellet of Example 6 shown in FIG. 2, as in the electron microscope photograph in FIG. 1 (Example 2), a sea/island/island structure is formed in which the polyethylene terephthalate resin and the polyphenylene ether resin are both dispersed as islands in the sea of the polycarbonate resin. The polyphenylene ether resin is dispersed in the polycarbonate resin, in the shape of an ellipse to a nearly perfect circle having a maximum diameter exceeding 3 μm.

In the electron microscope photograph of the pellet of Comparative Example 4 shown in FIG. 3, a sea/island structure is formed in which the polyethylene terephthalate resin is dispersed as islands in the sea of the polycarbonate resin. No polyphenylene ether resin is observed which is dispersed without surrounding an aggregate of plate-shaped fillers, and these are different from the observation in the electron microscope photographs in FIGS. 1 and 2.

As to sizes of the gray portions 2 that contain the polyethylene terephthalate resin, and may include an aggregate 4 of plate-shaped fillers, FIG. 1 and FIG. 3 are compared. It is clear that the gray portions 2 in FIG. 1 have greater sizes. Such a difference in size of the gray portion 2 may be attributed to the presence or absence of the polyphenylene ether resin. In addition, the sizes of the gray portion 2 in the present invention may have a factor of achieving the advantages of the present invention.

DESCRIPTION OF THE REFERENCE CHARACTERS

1 polycarbonate resin
2 thermoplastic polyester resin
3 polyphenylene ether resin
4 mica

The invention claimed is:

1. A polycarbonate resin composition comprising: 100 parts by weight of a resin component containing not less than 35 wt % and not more than 95 wt % of a polycarbonate resin (A), and not less than 5 wt % and not more than 65 wt % of a thermoplastic polyester resin (B); not less than 1 part by weight and not more than 20 parts by weight of an amorphous thermoplastic resin (C) having a glass transition temperature of not lower than 110° C.; and not less than 1 part by weight and not more than 50 parts by weight of plate-shaped fillers (D) having a number average major axis length of not less than 0.5 μm and not more than 45 μm.

2. The polycarbonate resin composition according to claim 1, wherein the amorphous thermoplastic resin (C) is incompatible with the polycarbonate resin (A) and is incompatible with the thermoplastic polyester resin (B).

3. The polycarbonate resin composition according to claim 1, wherein the amorphous thermoplastic resin (C) is at least one amorphous resin selected from the group consisting of polyphenylene ether resins, polyarylate resins, polyetherimide resins, polysulfone resins, and modified styrene resins.

4. The polycarbonate resin composition according to claim 1, wherein the polycarbonate resin composition has a deflection temperature under load of not lower than 110° C. and not higher than 120° C.

5. The polycarbonate resin composition according to claim 1, wherein the polycarbonate resin composition has a weight reduction start temperature of not lower than 410° C. and not higher than 420° C. as measured using a differential thermal/thermogravimetric simultaneous measurement device.

6. A molded article comprising the polycarbonate resin composition according to claim 1.

7. The molded article according to claim 6, wherein the molded article has a maximum projected area of not less than 10,000 mm$^2$ and not more than 10,000,000 mm$^2$.

* * * * *